US006815682B2

United States Patent
Rabinovich et al.

(10) Patent No.: US 6,815,682 B2
(45) Date of Patent: Nov. 9, 2004

(54) INFRARED SENSING OF CONCENTRATION OF METHANOL'S AQUEOUS SOLUTION

(75) Inventors: Arnold Rabinovich, Cary, NC (US); Evangelos Diatzikis, Apex, NC (US); Jeffrey Mullen, Apex, NC (US); Daryl Tulimieri, Raleigh, NC (US)

(73) Assignees: E. I. du Pont de Nemours and Company, Wilmington, DE (US); ABB Research Ltd., Zurich (CH)

( * ) Notice: Subject to any disclaimer, the term of this patent is extended or adjusted under 35 U.S.C. 154(b) by 502 days.

(21) Appl. No.: 10/033,709

(22) Filed: Dec. 28, 2001

(65) Prior Publication Data

US 2003/0124398 A1 Jul. 3, 2003

(51) Int. Cl.[7] ............................................. G01N 33/20
(52) U.S. Cl. ................................ 250/338.5; 250/339.09
(58) Field of Search ........................... 250/338.5, 343, 250/339.09, 339.11, 339.12; 356/128; 73/61.45, 61.49, 597; 429/17, 42, 92; 324/431; 204/422; 205/783.5, 787; 340/632

(56) References Cited

U.S. PATENT DOCUMENTS

| | | | | |
|---|---|---|---|---|
| 5,126,570 A | * | 6/1992 | Boos | 250/343 |
| 5,176,320 A | | 1/1993 | Kraus et al. | 239/2.2 |
| 5,750,995 A | * | 5/1998 | Clarke | 250/339.12 |
| 5,773,162 A | * | 6/1998 | Surampudi et al. | 429/39 |
| 5,868,859 A | | 2/1999 | Hei et al. | 134/18 |
| 6,067,840 A | | 5/2000 | Chelvayohan et al. | 73/23.2 |
| 6,120,925 A | * | 9/2000 | Kawatsu et al. | 429/40 |
| 6,254,748 B1 | * | 7/2001 | Surampudi et al. | 204/422 |
| 6,306,285 B1 | | 10/2001 | Narayanan et al. | 205/787 |
| 6,308,572 B1 | | 10/2001 | Ishikawa et al. | 73/597 |
| 6,549,276 B1 | * | 4/2003 | Longtin | 356/128 |
| 6,748,793 B2 | * | 6/2004 | Rabinovich et al. | 73/61.45 |
| 2003/0196913 A1 | * | 10/2003 | Xie et al. | 205/787 |
| 2003/0198852 A1 | * | 10/2003 | Masel et al. | 429/30 |

OTHER PUBLICATIONS

Perkin–Elmer Ltd, "Horizontal ATR Accessory," *Perkin–Elmer Spectrum 2000 FT–IR Manual*, 1995, 1–11.

* cited by examiner

*Primary Examiner*—Constantine Hannaher
*Assistant Examiner*—Otilia Gabor (57) ABSTRACT

Systems and methods for infrared sensing a compound's concentration in aqueous solution are provided. In various non-limiting embodiments, the invention provides infrared sensing of methanol's concentration in aqueous solution in connection with a fuel circulation process for a direct methanol fuel cell. In some embodiments, flow-through infrared sensing technique are provided. In other embodiments, window type infrared sensing techniques are provided. As a result of the infrared sensing, an accurate real-time measurement of the concentration of a compound of interest in aqueous solution is affordably obtained.

22 Claims, 8 Drawing Sheets

INFRARED SENSING OF CONCENTRATION OF METHANOL'S AQUEOUS SOLUTION

FIELD OF THE INVENTION

The present invention relates generally to the field of sensing the concentration of an aqueous solution. More particularly, the present invention relates to infrared sensing of the concentration of methanol's aqueous solution in connection with a fuel circulation loop of a direct methanol fuel cell.

BACKGROUND OF THE INVENTION

A direct methanol fuel cell (DMFC) is a type of polymer electrolyte membrane fuel cell (PEMFC). A DMFC operates at low internal temperature (~80 C.) and fuel is a non-flammable dilute methanol/water mixture, closely approximating auto windshield wiper fluid. There are no Environmental Protection Agency (EPA) regulated emissions in connection with using a DMFC, allowing for continuous operation. By some estimates, projected engineering power density for DMFCs is 10–20 Watts per liter.

PEMFCs, such as DMFCs, provide low temperature operation, cleanliness, safety, quiet performance, ease of operation, low maintenance, portability, modularity, scalability, responsiveness and versatility. The 'direct' aspect of DMFCs implies the elimination of a fuel reformer component, which simplifies the overall fuel system, lowering cost, making for a smaller assembly and further increasing efficiency. Due to the versatility of DMFCs, they may be used, e.g., to power transceiver stations for remote mobile telecommunications systems, to provide backup power to telecommunications systems and to provide remote residential power, among a myriad of other applications. Thus, DMFCs are capable of providing reliable and affordable power in remote locations. From an efficiency standpoint, current DMFC performance yields approximately 1 kilowatt average load for 3 months using about 500 gallons of fuel. Moreover, significant advances are expected in the near future increasing efficiency even further, bringing DMFCs ever closer to the forefront of power technology.

During operation of a fuel circulation loop for a DMFC, methanol and water are mixed in a fuel mixer, and it is important to the process that the concentration of methanol aqueous solution remains reasonably controlled throughout operation of the DMFC. In this regard, the rate by which methanol is added to the system is related to the rate of depletion of methanol in the system and thus, sensing the concentration of methanol so that an appropriate amount of methanol can be metered is desirable for such a process. Accordingly, there is a need for accurate measurement of fuel concentration in such a fuel cell system.

U.S. Pat. No. 6,306,285, to Narayanan et al., entitled "Techniques for Sensing Methanol Concentration in Aqueous Environments" (the '285 patent) discloses a technique for sensing methanol concentration, and provides a methanol concentration sensor device for coupling to a fuel metering control system for use in a liquid direct-feed fuel cell.

The method of the '285 patent teaches detecting a methanol compound concentration in an aqueous environment by using a sensor element to probe a liquid analyte solution including methanol to produce a sensor response. The sensor element includes an anode, a solid electrolyte membrane and a cathode. The sensor element also includes a catalyst, which is capable of chemically reacting with methanol. According to the method, the anode and cathode of the sensor element are immersed in the liquid analyte solution. An electrical power supply's positive terminal is connected to the anode and the electrical power supply's negative terminal is connected to the cathode. An analyte concentration sensing device is connected to the sensor element for detecting the response to the analyte, and is also connected electrically to the sensor element and the power supply in order to detect an amount of current consumed thereby. The method is alleged to be reliable in aqueous environments in the analyte concentration range 0.01 M to 5 M, and a temperature range of 0°–100° Celsius.

The sensors of the '285 patent, however, are relatively slow due to the time for the reactions to take place in the analyte solution. The need for a fast view of macroscopic change in concentration of methanol solution is thus undermined by the method taught by the '285 patent. Additionally, the sensor of the '285 is sensitive to both metallic and biological contaminants, skewing results undesirably. Since these contaminants further affect the operation of the DMFC itself due to a similar anode/cathode mechanism, over time, the use of the sensor of the '285 fails to serve as an impartial diagnostic tool. Moreover, additional plumbing and components are required that make such an implementation complex. For example, separate plumbing must be provided to the fuel samples and separate oxygen feed.

There are also other exhaustive techniques that are capable of measuring the concentration of methanol at a very high resolution. Since these techniques reproduce one or another principle of measurement of absolute physical value connected to absolute value of concentration, they are expensive and cumbersome, and thus not affordable and simple.

Thus, there is currently a strong need in the art for an improved system and methods for measuring the methanol-water mixture concentration accurately for a stand-alone DMFC. In this regard, there is a need in the art for simple, affordable and reliable methods for measuring methanol's concentration in aqueous solution in a DMFC fuel circulation loop.

SUMMARY OF THE INVENTION

In view of the foregoing, the present invention provides systems and methods for infrared sensing a compound's concentration in aqueous solution. In various non-limiting embodiments, the invention provides infrared sensing of methanol's concentration in aqueous solution in connection with a fuel circulation process for a direct methanol fuel cell. In some embodiments, flow-through infrared sensing techniques are provided. In other embodiments, window type infrared sensing techniques are provided. As a result of the infrared sensing, an accurate real-time measurement of the concentration of a compound of interest in aqueous solution is affordably obtained.

Other aspects of the present invention are described below.

BRIEF DESCRIPTION OF THE DRAWINGS

The methods for sensing the concentration of methanol's aqueous solution with infrared light are further described with reference to the accompanying drawings in which.

DETAILED DESCRIPTION OF THE INVENTION

Overview

Figure 1A:
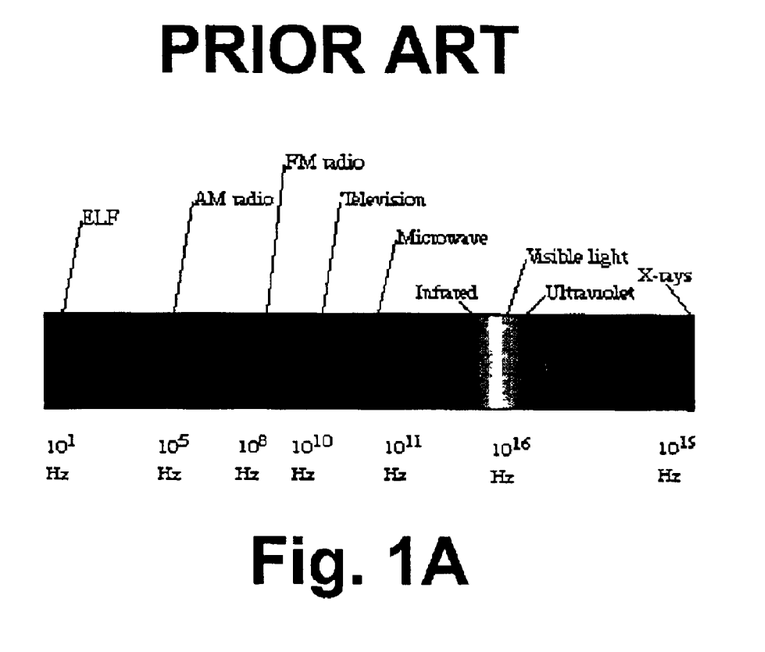
FIG. 1A illustrates the position of infrared radiation in the electromagnetic spectrum.

No present system exists for measuring the concentration of methanol's aqueous solution by utilizing infrared (IR) light in a way that is simple, inexpensive and reliable. As depicted in FIG. 1A, infrared radiation is the region of the electromagnetic spectrum between microwaves and visible light. Generally speaking, an IR source signal transmits non-visible infrared light. At the receiving end, which may also be the transmitting end upon reflection of the infrared light, a photodetector captures the light, which is then processed to retrieve the information the light carries.

The use of infrared light has a variety of known advantages. Infrared is advantageous because one can use a variety of publicly available transmitters and receivers. Infrared systems are secure because infrared signals do not penetrate walls, and there is no risk of injury, except for applications employing extremely intense and focused infrared beams. Additionally, with the exception of high frequency lights and bright sunlight, there are few sources of interference with infrared systems, such as interference from electromagnetic interference (EMI) and radio frequency (RF) signals. Furthermore, infrared systems implicate desirably low power requirements and low circuitry costs for operation; plus, the relatively simple circuitry requires no special or proprietary hardware, such that the circuitry can be easily incorporated into a larger integrated circuit package. Still further, the directionality of an infrared beam helps ensure that data isn't leaked or spilled to nearby devices as the light is transmitted.

In view of the advantages provided by the use of infrared light, the present invention provides methods of infrared sensing the concentration of methanol's aqueous solution in connection with the fuel circulation loop of a DMFC in a way that is simple, affordable and reliable. It is understood that the techniques described herein may be applied to any application relating to the monitoring of small changes in concentration of a component of a liquid system that leads to an observable change of the amplitude of absorption in a specific band of the IR spectrum.

Methanol Concentration Sensing

Concentration of methanol-water fuel solution circulating through the DMFC changes during the work process at a rate dependent on several factors, such as electrical load and temperature, resulting in a non-uniform consumption of methanol from the fuel solution. Therefore, monitoring of fuel concentration and control of its value are continuous during operation of DMFC. Due to relatively slow changes of concentration, measurements and controlling may be done within a sampling cycle in a range of 1 change in 1 minute. This frequency is enough for full cycle measurement and control of the methanol concentration, although it is understood that achieving a better, faster rate provides optimization benefits in terms of a simpler physical construction of the DMFC assembly as well as in terms of streamlining the operation of the DMFC. Additionally, in order to provide effective control of the fuel circulation loop for a DMFC, the resolution of the sensor must be in the neighborhood of 0.1 weight % or better, since that is the level of control that is required to maintain a proper fuel mixture for the operation of a DMFC. The sensor device that achieves this resolution in accordance with the techniques of the present invention may be provided as part of a DMFC assembly.

Figure 1B:
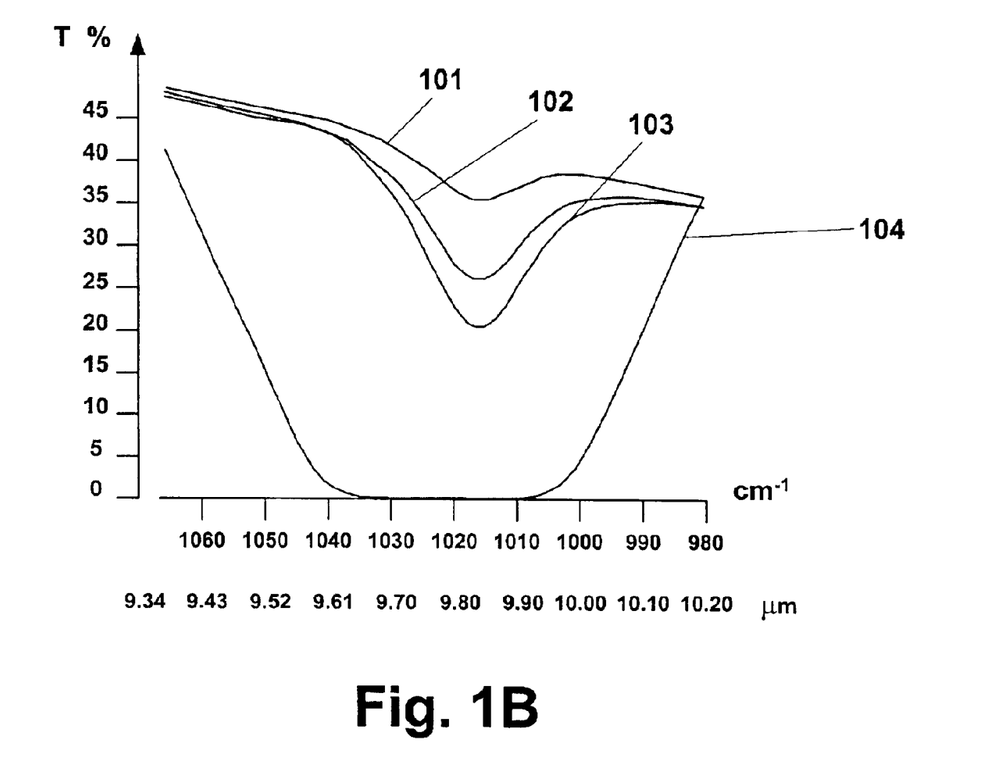
FIG. 1B illustrates experimental results showing the uniqueness of peak absorption in Fourier transform infrared (FTIR) spectra curves for low concentrations of methanol in aqueous solution relative to a reference curve for pure methanol.

The infrared sensor utilized in accordance with the methods of the present invention is based on a principle of selective absorption of IR radiation, i.e., IR spectroscopy. When a beam of IR radiation is passed through a medium, the emerging beam is diminished in intensity at a certain wavelength indicating its absorption by the medium. The pattern of absorption spectrum of IR radiation of a particular substance is distinctly characteristic of that substance and hence can be used to identify that substance and its concentration in the medium in comparison with the absorption spectrum of a reference substance. FIG. 1B illustrates the results of an experiment, which shows that, in the far infrared region, diluted aqueous solutions of methanol, e.g., 1% methanol by volume curve 101, 3% methanol by volume curve 102 and 5% methanol by volume curve 103, have associated distinct absorption peaks in their respective absorption spectrum curves as compared to the absorption spectrum curve 104 of pure methanol.

As can be seen from FIG. 1B, the magnitude of absorption is proportional to the concentration of methanol in water, which is instrumental for obtaining numerical data. Such quantitative spectroscopic analysis is a well known tool in analytical chemistry. It allows detection of infinitesimal amount of a substance in various states—gas, solids, and liquids. Although contemporary IR spectroscopy can be an extremely sophisticated optical and electronic instrument, the present invention reproduces this technique with substantial simplifications. For example, the infrared device(s) utilized in accordance with the present invention are made for one chosen waveband. Thus, there is no need for wavelength tuning of the IR source or receiver. Also, an interference type filter with a given wavelength and bandwidth may be an appropriate substitute for complicated monochromators.

The present invention is directed to methods for using an infrared sensor device for measuring methanol's content in water solutions in the fuel circulation loop of a DMFC. The infrared sensor is designed based on a specific methanol absorption peak in the infrared range. As shown by FIG. 1B, the IR spectrum of aqueous solution of methanol shows a well-distinguished absorption peak at a wavelength of about 9.85 micrometers. The amplitude of the absorption peak is proportional to methanol concentration. The present invention is proven effective for measuring the concentration of methanol in the range 0% to 5% in water solution as a fuel in a DMFC. Similar infrared measuring may be achieved for any percentage range for which distinguishable peaks are observable in the associated IR spectrum curves.

Two types of sensors are described herein, along with accompanying methods of use. The first type of sensor is a flow-through sampling cell, comprised of two IR-transparent germanium (Ge) plates with band filters deposited on the outer surfaces of the plates. A polymer thin film spacer-sealer is shaped so that it creates two identical flat cavities for a sample liquid and reference liquid. A system of micro-tubes is also in place for the flow through sampling solution and reference liquid. A pair of IR-receivers e.g., pyroelectric detectors, are located in front of the centers of the sample cavity and the reference cavity and are electrically connected to two symmetrical inputs of an instrumental amplifier, the output of which serves as an analog output of the device.

The second type of detector is a window type detector. A window type detector is comprised of a Ge total reflectance crystal with band filters deposited on its input and output bevels, and a pyroelectric detector as a receiver.

A miniature IR emitter serves as a source in both flow-through and window types. The infrared devices and methods for using the same described herein provide low power consumption, compact instrumentation for determining the percentage concentration with a simple electrical analog output and can be used as a methanol concentration sensor in fuel cell systems. The analog output of the sensors can be analyzed directly or digitized and analyzed by a computing device, such as a microprocessor designed for the task. An output of the microprocessor based on the analog output may then be utilized as an input to the fuel circulation loop for controlling the amount of methanol being mixed in real-time.

Flow-Through Type Sensor

Figure 2:
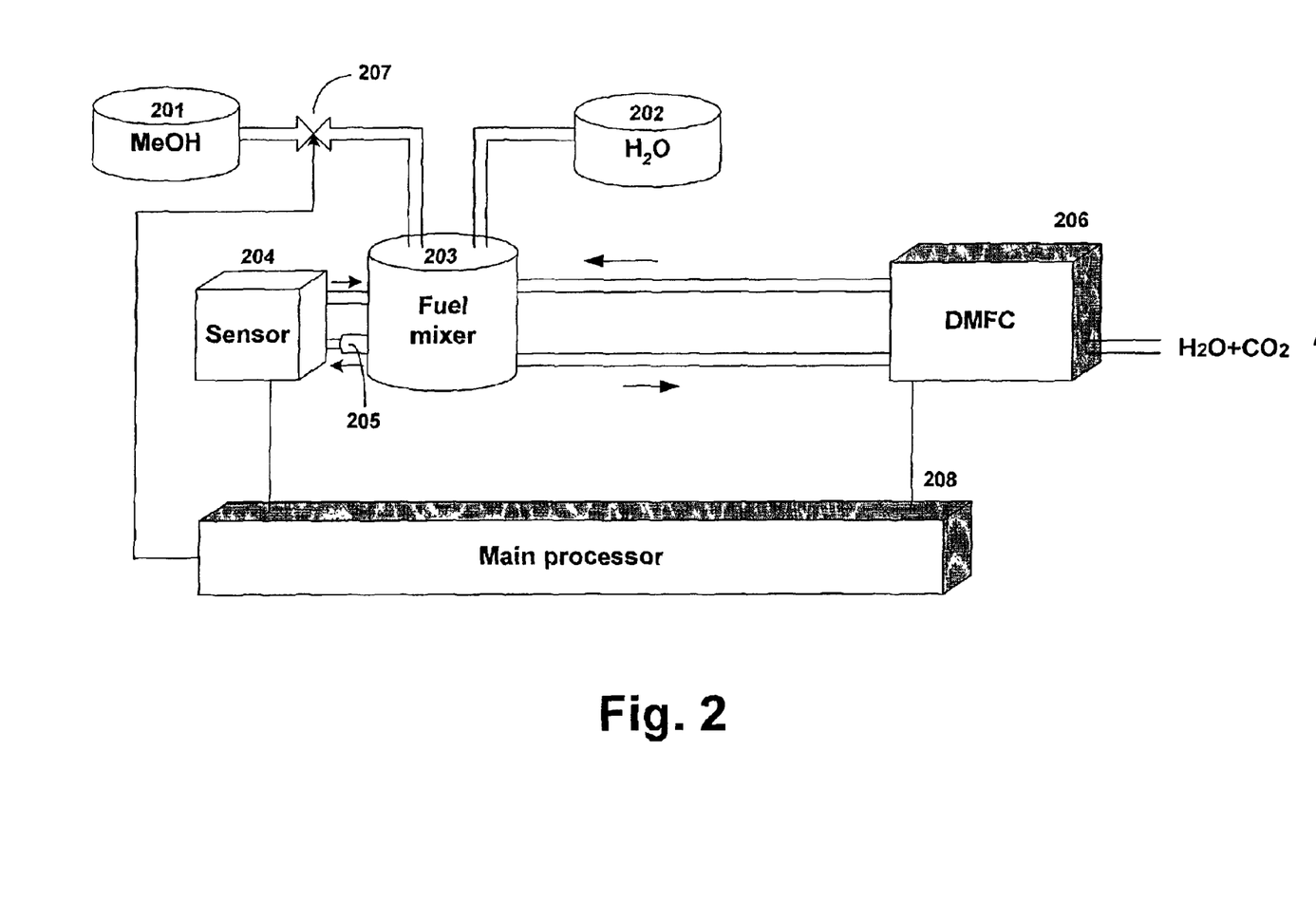
FIG. 2 is a diagram of a fuel circulation process having a first type of infrared sensing in accordance with the present invention.

As mentioned above, two types of sensors are considered in accordance with the present invention. The first type is flow-through. The location of this sensor in the DMFC layout may be understood from general diagram of FIG. 2. In FIG. 2, methanol, or MeOH, stock 201 and $H_2O$ stock 202 are mixed together in fuel mixer 203, whereby the flow controller 207 regulates the amount of methanol injected to the mix based on an input from the control processor 208. DMFC 206 partially consumes the fuel from fuel mixer 203, producing byproducts $H_2O$ and $CO_2$ and returning a fuel solution of unknown methanol concentration to fuel mixer 203. Sample fuel from fuel mixer 203 is input to sensor 204 via flow matching link 205. Sensor 204 then utilizes infrared sensing techniques to compare an infrared measurement of the sample fuel to an infrared measurement of a reference liquid, such as pure water, and outputs a signal representative of the relevant portion of the FTIR spectrum for the sample fuel. This signal is an input to the main processor 208, which interprets the signal in terms of the methanol concentration of the fuel mix in the fuel mixer 230. Main processor 208 then outputs a corresponding control signal to the flow controller 207 based on the current consumption needs of DMFC 206.

Figure 3:
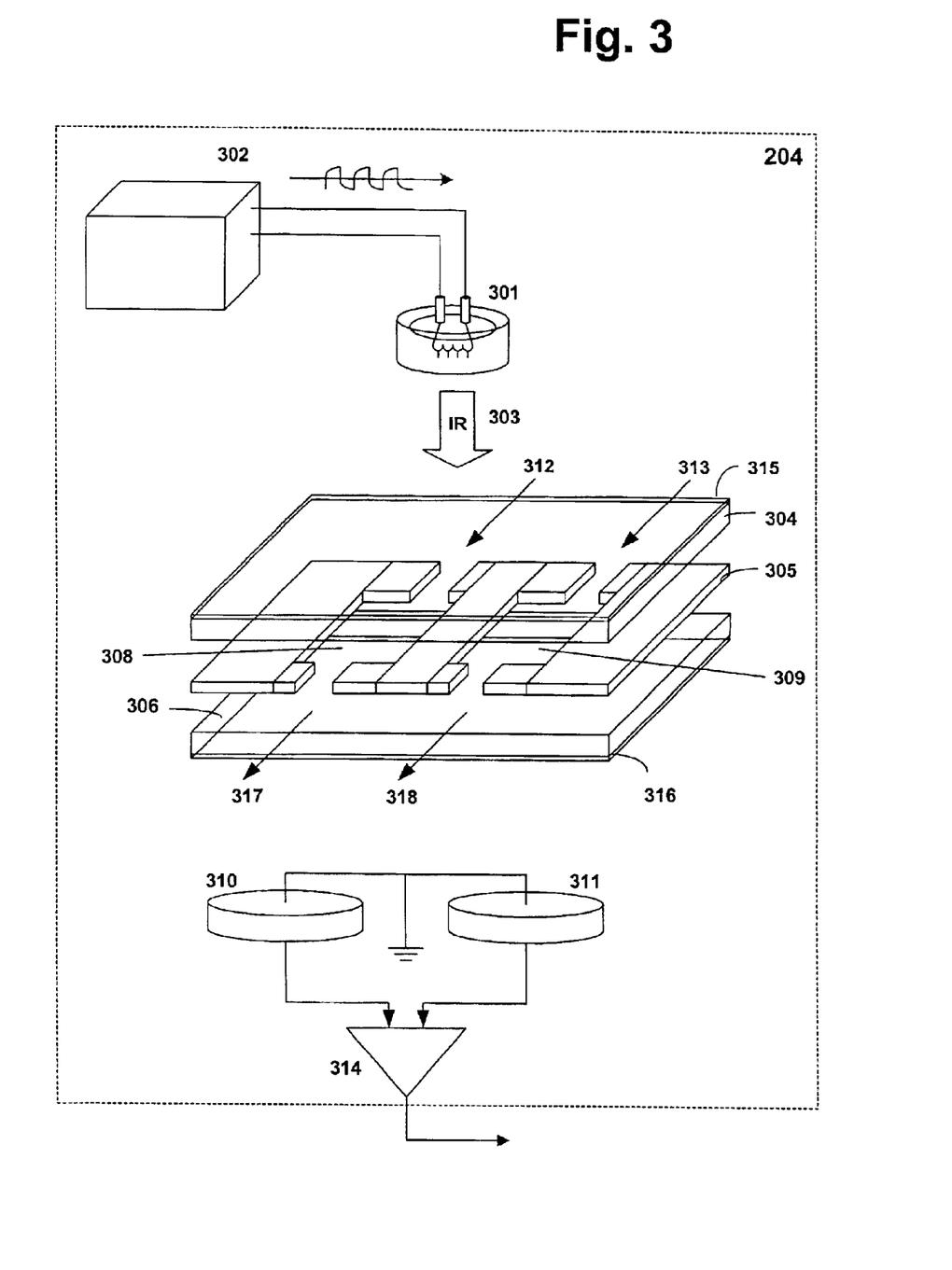
FIG. 3 is a diagram of the first type of infrared sensing in exemplary detail in accordance with the present invention.

A more detailed view of the operation of flow-through IR sensor 204 is depicted in FIG. 3. In FIG. 3, a low frequency alternating current (AC) source 302 powers narrow band IR emitter 301, which emits IR light 303 towards interference type thin layer 315 on upper plate 304. Between upper plate 304 and lower plate 306 is spacer(s) 305. Through sample cell 308 flows the fuel mix sample from 312 to 317 and through standard cell 309 flows the reference sample, such as pure water, from 313 to 318. The IR light irradiates both the sample cell 308 and standard cell 309 and transmits through lower plate 306 and interference type thin layer 316. The IR light transmitted through sample cell 308 is received by IR detector 310 and the IR light transmitted through standard cell 309 is received by IR detector 311, which detectors 310 and 311 then output corresponding detection signals to instrumental amplifier 314. Instrumental amplifier 314 outputs a signal based upon the inputs from detectors 310 and 311, which signal is then input to main processor 208 of FIG. 2.

The selectivity to the specific wavelength in sensor 204 is due to thin layer filters 315 and 316 that are deposited on the outer surfaces of the plates 304 and 306. The plates themselves are made from Ge single crystal. They can be made from other material, which is transparent enough for IR in the range of $\lambda=10\,\mu m$. The choice of Ge in this embodiment followed from its compatibility to a mixture of $MeOH/H_2O/CO_2$ at an elevated temperature. The two thin identical cells 308 and 309 are formed as the voids in 25 $\mu m$ thick polymer spacer 305. The sample liquid flows through the flat thin cell 308 in the direction shown by the arrows 312 and 317. Similarly, the standard liquid, e.g., pure deionized water, flows through the cell 309, as shown by the arrows 313 and 318. The rate of both flows is sufficient for full exchange of liquids within the time domain typical for the possible change of $MeOH/H_2O$ concentration in the fuel feed loop. This differential design enhances noise immunity of the detection and simplifies signal processing in terms of temperature corrections.

Window Type Sensors

Figure 4A:
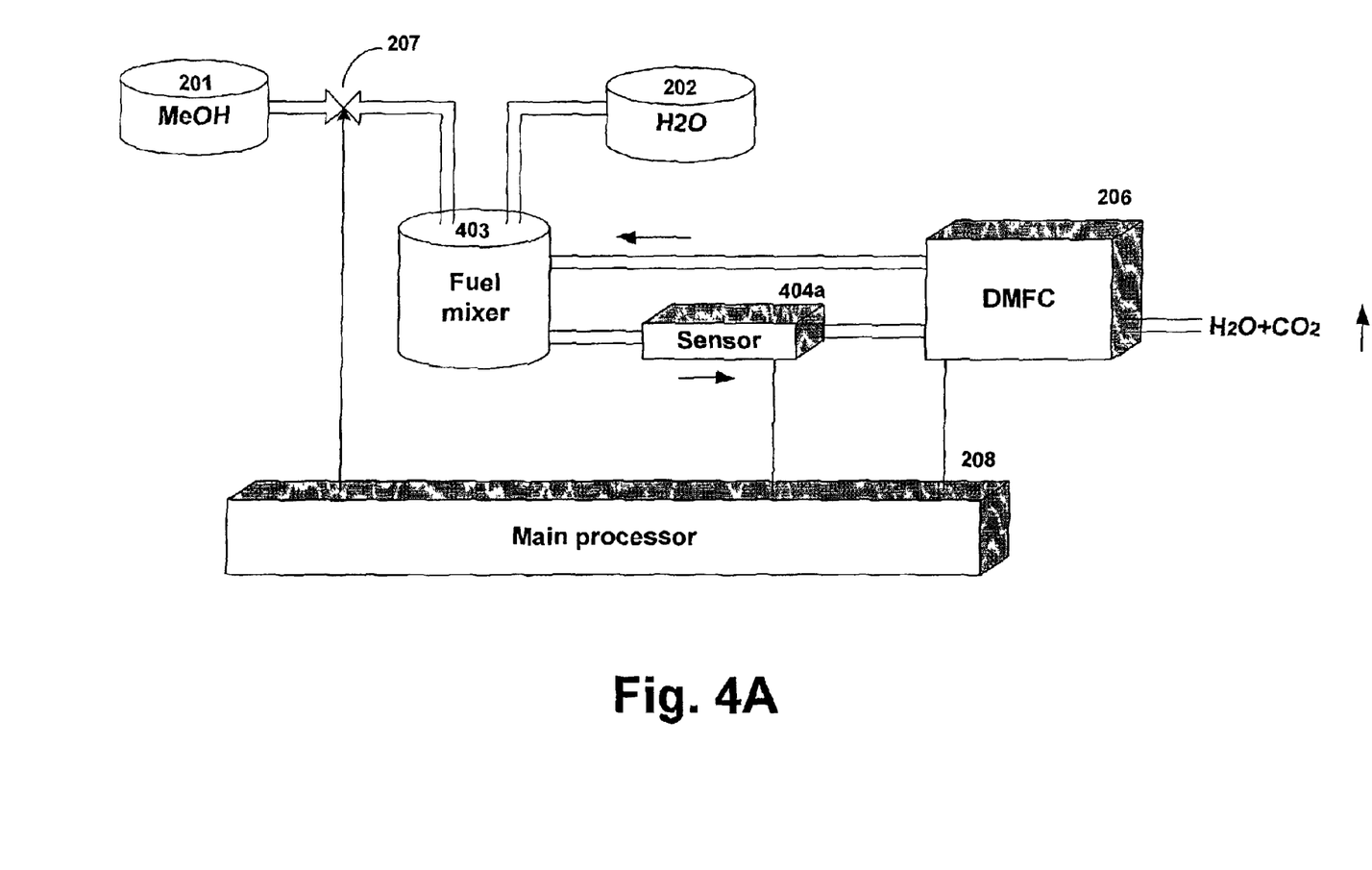
FIGS. 4A and 4B are diagrams of a fuel circulation process having a second type of infrared sensing in accordance with the present invention.
Figure 4B:
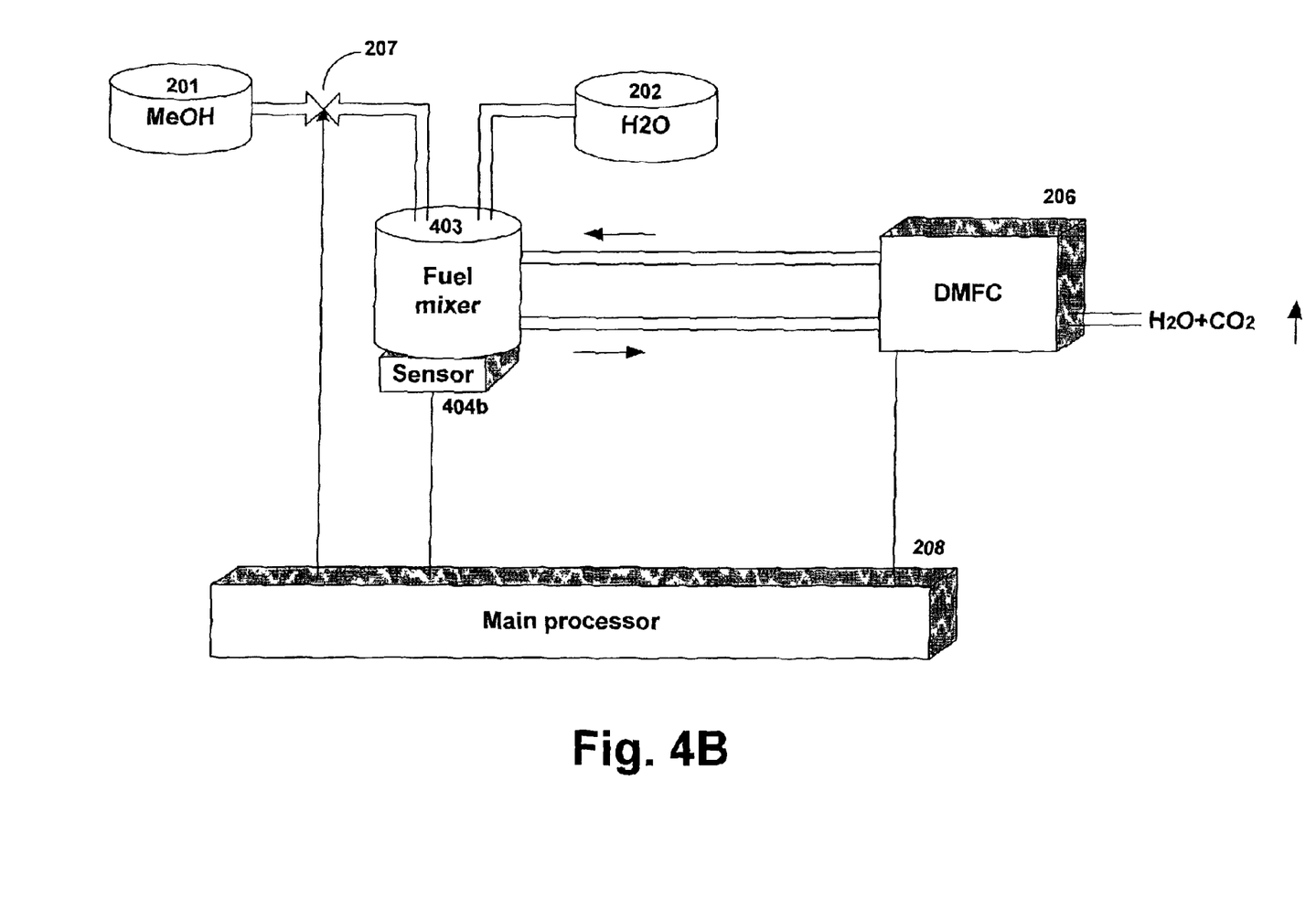

General diagrams of fuel control for the second, window type sensor are depicted in FIGS. 4A and 4B. In FIGS. 4A and 4B, as with FIG. 2, MeOH stock 201 and $H_2O$ stock 202 are mixed together in fuel mixer 403, whereby the flow controller 207 regulates the amount of methanol injected to the mix based on an input from the control processor 208. DMFC 206 partially consumes the fuel from fuel mixer 203, producing byproducts $H_2O$ and $CO_2$ and returning a fuel solution of unknown methanol concentration to fuel mixer 203.

In the embodiment of FIG. 4A, however, a window type sensor 404a is positioned along the fuel path from fuel mixer 403 to DMFC 206. Sensor 404a utilizes infrared sensing techniques to output a signal representative of the relevant portion of the FTIR spectrum for the fuel actually being input to DMFC 206. This signal is an input to the main processor 208, which interprets the signal in terms of the methanol concentration of the fuel mix in the fuel mixer 403. Main processor 208 then outputs a corresponding control signal to the flow controller 207 based on the current consumption needs of DMFC 206.

For the flow-through type sensor 204 of FIG. 2, which requires only a small amount of sample fuel, a device 205 for flow adjustment is installed between the sensor feeding line and fuel mixer 203, while the window sensor 404a can be positioned as an in-line type directly in the fuel feeding line. As illustrated by FIG. 4B, a window sensor 404b may be attached to or formed as part of the fuel mixer 403 itself.

Figure 5A:
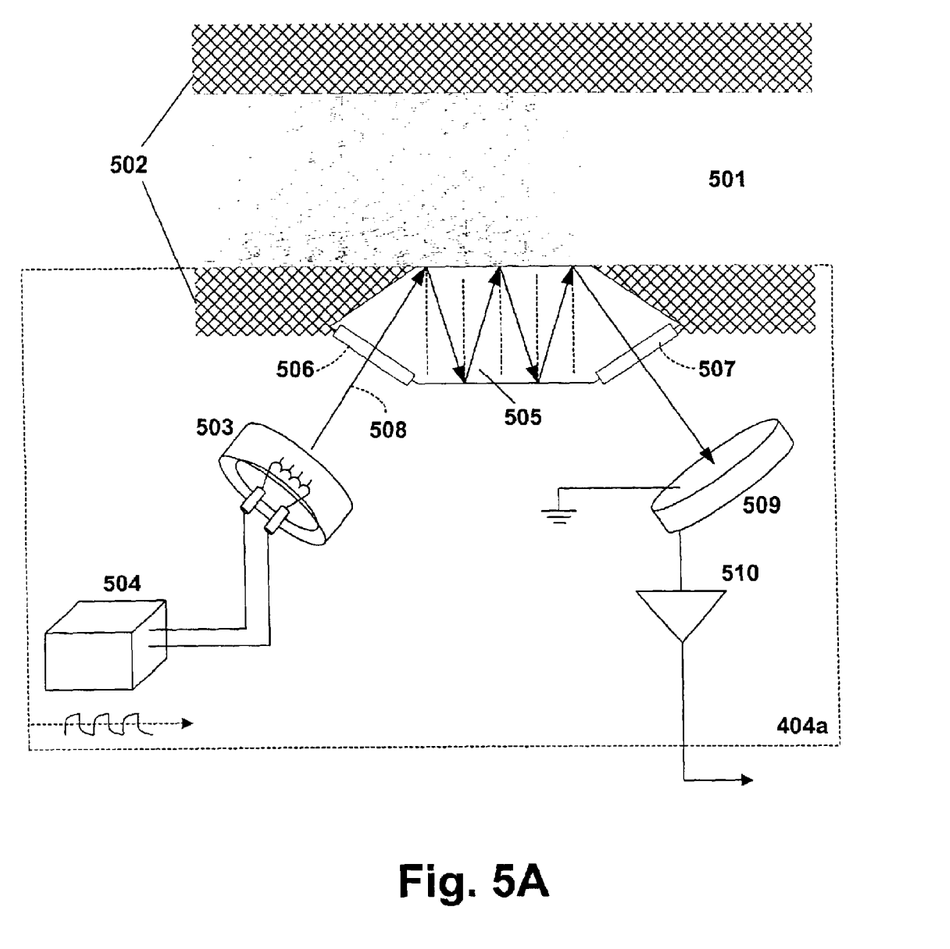
FIGS. 5A and 5B are diagrams of the second type of infrared sensing in exemplary detail in accordance with the present invention.
Figure 5B:
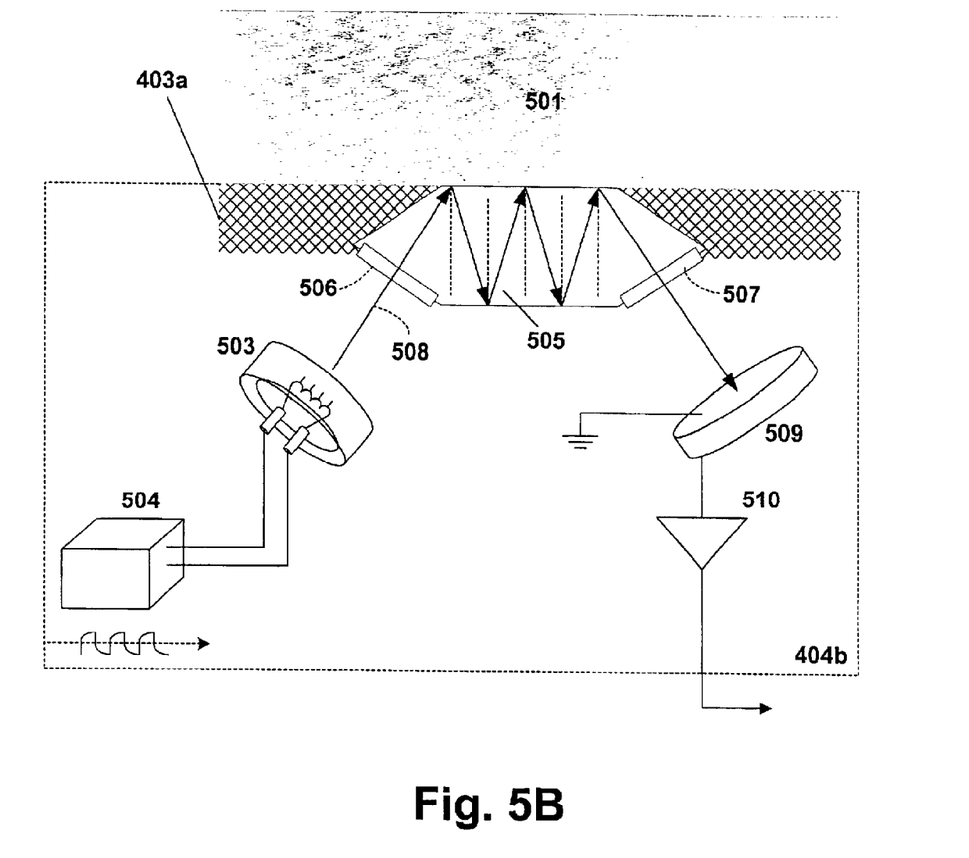

The window type sensors 404a or 404b deploy an attenuated total reflectance (ATR) method. FIGS. 5A and 5B illustrate an exemplary implementation of the ATR method for the window type sensors 404a and 404b, respectively. With reference to FIG. 5A, the method for infrared sensing the concentration of methanol's aqueous solution proceeds in an exemplary manner as follows for a window type sensor 404a. For example, window type sensor 404a is positioned on, or in, a wall 502 of the fuel line carrying $MeOH/H_2O$ fuel 501. Sensor 404a includes a narrow band IR source 503, which is powered by a low frequency AC source 504, which emits IR light 508 through thin layer filter 506 into Ge total reflectance crystal medium 505. IR radiation 508 then reflects back and forth through medium 505 until the light escapes through thin layer filter 507 and is received by IR detector 509. IR detector 509 outputs its detection signal to amplifier 10, and amplifier 10 outputs a signal to main processor 208 as illustrated in FIG. 4A.

In order to have immediate contact between IR radiation 508 and liquid $MeOH/H_2O$ fuel 501, the window type sensor 404a is manufactured to be part of the fuel feeding line. The sensitivity and noise immunity of window type sensor 404a depends on the effective path length of IR waves. The effective path length, in turn, is equal to the product of the number of reflections in the "liquid-crystal" interface 505 and the depth of penetration (dp) according to the following relation:

$$dp = \lambda/2\pi * n_c * [\sin^2 \theta - (n_s/n_c)^2]^{1/2}$$

where θ is the crystal face angle, $n_c$ is the refractive index of crystal 505, and $n_s$ is the refractive index of a liquid fuel sample. For Ge, $n_c$=4, and for MeOH/H$_2$O, $n_s$ is approximately 1.33.

For instance, if θ=45° and λ=10 μm, the depth of penetration is approximately 0.6 μm. To obtain appropriate absorption with a dp value in this range, the number of reflections is generally optimized to be about 10 to 15. In one implementation, this is achieved with inexpensive Ge single crystal with dimensions: 4 to 5 mm thickness and 20 to 25 mm in diameter.

For window type sensor 404b, as illustrated by FIGS. 4B and 5B, the sensor may be attached to a wall 403a of the fuel mixer 403 itself, i.e., underneath the fuel mixer 403, to the side of the fuel mixer 403, as part of the fuel mixer 403, etc., and thus the same techniques may be applied.

Conclusion

While the present invention has been described in the context of measuring methanol's concentration in aqueous solution in connection with a DMFC fuel circulation process, the methods of the present invention can be used for any application related to monitoring small changes of concentration of a component of a liquid system, wherein the small changes lead to a corresponding change in the amplitude of absorption in a specific band of the IR spectrum.

It is understood that the methods and apparatus of the present invention may be implemented in many different forms. Thus, the present invention is by no means limited to any particular form of stock container 201 or 202, fuel mixer 203, DMFC 206, processor 208, flow controller 207, IR sources 301 and 503, IR detectors 310, 311 and 509 and so on. Moreover, it is apparent that the present invention may be practiced without necessarily using all of these components, or by replacing some or all of these with functional equivalents. Accordingly, the scope of protection of the following claims is not intended to be limited to the presently preferred embodiments described herein.

What is claimed is:

1. A method for flow-through infrared sensing the concentration of methanol in aqueous solution in connection with a fuel circulation loop of a direct methanol fuel cell, comprising:
   transmitting infrared light through a fuel sample and a reference liquid;
   receiving the infrared light that is not absorbed by the fuel sample and reference liquid by first and second infrared detectors, respectively;
   outputting a signal based upon the infrared light received by the first and second infrared detectors; and
   processing the signal with a processor to determine the concentration of methanol in the fuel sample.

2. A method according to claim 1, further including controlling the flow rate of methanol into a fuel mixer based upon the determined concentration.

3. A method according to claim 1, wherein the reference liquid is water.

4. A method according to claim 1, wherein the reference liquid is a fixed known concentration of methanol in water.

5. A method according to claim 1, wherein said transmitting includes transmitting said infrared light through a thin interference layer.

6. A method according to claim 1, wherein said transmitting includes transmitting narrow band infrared light.

7. A flow-through infrared sensor system for sensing the concentration of methanol in aqueous solution in connection with a fuel circulation loop of a direct methanol fuel cell, comprising:
   an infrared source for transmitting infrared light through a fuel sample and a reference liquid;
   a first infrared detector for receiving the infrared light that is not absorbed by the fuel sample
   a second infrared detector for receiving the infrared light that is not absorbed by the reference liquid;
   means for outputting a signal based upon the infrared light received by the first and second infrared detectors; and
   a processor for processing the signal to determine the concentration of methanol in the fuel sample.

8. A system according to claim 7, further including a flow rate controller that controls the flow rate of methanol into a fuel mixer based upon a control signal output by the processor after the processor determines the concentration of methanol in the fuel sample.

9. A system according to claim 7, wherein the reference liquid is water.

10. A system according to claim 7, wherein the reference liquid is a fixed known concentration of methanol in water.

11. A system according to claim 7, wherein the infrared light is transmitted through a thin interference layer.

12. A system according to claim 7, wherein the infrared source transmits narrow band infrared light.

13. A method for window type infrared sensing the concentration of methanol in aqueous solution in connection with a fuel circulation loop of a direct methanol fuel cell, comprising:
   positioning a window type infrared sensor such that a window surface of the sensor is in contact with a fuel sample;
   transmitting infrared light through a first opening of the sensor into a reflectance crystal medium of the sensor against the window surface at an angle, thereby reflecting the infrared light against the window surface and a wall of the sensor a plurality of times prior to the infrared light exiting the medium through a second opening;
   receiving the infrared light that exits the second opening by an infrared detector;
   outputting a signal based upon the infrared light received by the infrared detector; and
   processing the signal with a processor to determine the concentration of methanol in the fuel sample.

14. A method according to claim 13, wherein the positioning includes one of (1) positioning the sensor in a wall of a fuel line, which inputs fuel to the direct methanol fuel cell and (2) positioning the sensor in the wall of a fuel mixer component that includes the fuel output to said fuel line.

15. A method according to claim 13, further including controlling the flow rate of methanol into a fuel mixer based upon the determined concentration.

16. A method according to claim 13, wherein said transmitting includes transmitting narrow band infrared light.

17. A method according to claim 13, wherein said transmitting includes transmitting the infrared light through a first thin layer filter included in the first opening and said infrared light exits said medium through a second thin layer filter included in said second opening.

18. A window type infrared sensor system for sensing the concentration of methanol in aqueous solution in connection with a fuel circulation loop of a direct methanol fuel cell, comprising:

a container having a fuel sample inside;

a window type infrared sensor comprising a first opening, a second opening, a reflectance medium, a window surface and a wall opposite said window surface, wherein said sensor is coupled to the container such that the window surface of the sensor is in contact with the fuel sample;

an infrared light source for transmitting infrared light through the first opening into the reflectance crystal medium against the window surface at an angle, thereby reflecting the infrared light against the window surface and the wall of the sensor a plurality of times prior to the infrared light exiting the medium through the second opening;

an infrared detector for receiving the infrared light that exits the second opening;

means for outputting a signal based upon the infrared light received; and a processor for processing the signal to determine the concentration of methanol in the fuel sample.

19. A system according to claim 18, wherein the container is one of (1) a fuel line that inputs fuel to the direct methanol fuel cell and (2) a fuel mixer component that includes the fuel that is output to said fuel line.

20. A system according to claim 18, further including a flow rate controller that controls the flow rate of methanol into a fuel mixer based upon a control signal output by the processor after the processor determines the concentration of methanol in the fuel sample.

21. A system according to claim 18, wherein the infrared source transmits narrow band infrared light.

22. A system according to claim 18, wherein said first opening includes a first thin layer filter and said second opening includes a second thin layer filter.

* * * * *